US007915425B2

(12) United States Patent
Veera Reddy et al.

(10) Patent No.: US 7,915,425 B2
(45) Date of Patent: Mar. 29, 2011

(54) PROCESS FOR THE PREPARATION OF LOSARTAN

(75) Inventors: Arava Veera Reddy, Hyderabad (IN); Siripalli Udaya Bhaskara Rao, Hyderabad (IN); Chinnapillai Rajendiran, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 449 days.

(21) Appl. No.: 11/991,123

(22) PCT Filed: Dec. 21, 2005

(86) PCT No.: PCT/IN2005/000431
§ 371 (c)(1),
(2), (4) Date: Feb. 27, 2008

(87) PCT Pub. No.: WO2007/026375
PCT Pub. Date: Mar. 8, 2007

(65) Prior Publication Data
US 2010/0222597 A1    Sep. 2, 2010

(30) Foreign Application Priority Data

Aug. 31, 2005  (IN) ........................... 1215/CHE/2005

(51) Int. Cl.
*C07D 257/04*    (2006.01)
*C07D 233/68*    (2006.01)
(52) U.S. Cl. .................................... 548/252; 548/333.5
(58) Field of Classification Search ................... 548/250, 548/252, 254
See application file for complete search history.

(56) References Cited

U.S. PATENT DOCUMENTS

| 4,820,843 A | 4/1989 | Aldrich |
| 4,874,867 A | 10/1989 | Aldrich |
| 4,879,186 A | 11/1989 | Lindmayer |
| 5,484,955 A | 1/1996 | Kato et al. |

FOREIGN PATENT DOCUMENTS

| EP | 0253310 A2 | | 1/1988 |
| EP | 0578125 A1 | | 1/1994 |
| WO | WO 2005/014602 | * | 2/2005 |
| WO | WO-2005014602 A1 | | 2/2005 |

OTHER PUBLICATIONS

Carini, D. et al, "Nonpeptide Angiotensin II Receptor Angagonists...", Journal Med. Chem., 1991, vol. 34, pp. 2525-2547.
Larsen, R.D. et al, "Efficient Synthesis of Losartan, A Nonpeptide Angiotension II . . . ", J. Org. Chem, 1994, vol. 59, pp. 6391-6394, American Chemical Society.

* cited by examiner

*Primary Examiner* — Kamal A Saeed
*Assistant Examiner* — Nyeemah Grazier
(74) *Attorney, Agent, or Firm* — IpHorgan Ltd.

(57) ABSTRACT

The invention relates to a improved process for the preparation of Losartan and its potassium salt, which comprises: (i) reacting bromo OTBN with BCFI in the presence of a base and a phase transfer catalyst to produce a cyano aldehyde; reacting the formed cyano aldehyde with sodium azide in the presence of tributyl tin chloride to produce aldehyde tetrazole; reducing the formed aldehyde tetrazole with sodium borohydride to produce Losartan; and, if desired, converting the formed Losartan to its potassium salt by known method.

11 Claims, No Drawings

PROCESS FOR THE PREPARATION OF LOSARTAN

FIELD OF THE INVENTION

The invention disclosed in this application relates to an improved process for the preparation of Losartan. Losartan and its potassium salt, having the formulae (1) & (2) respectively are angiotensin-II receptor (Type AT1) antagonists.

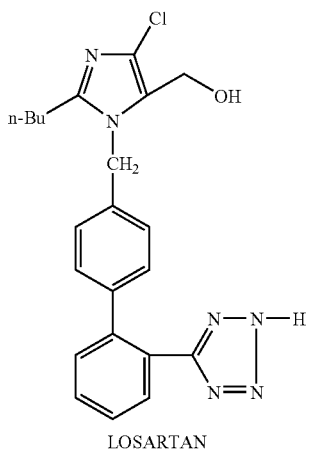

LOSARTAN

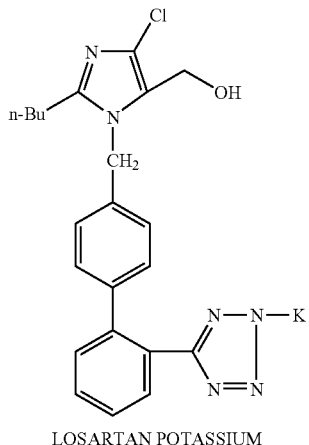

LOSARTAN POTASSIUM

In adults Losartan is currently indicated for the treatment of hypertension (in hypertensive patients with left ventricular hypertrophy, it is also indicated to reduce the risk of stroke).

BACKGROUND

Losartan Potassium having the formula 2 and its principle active metabolite block the vasoconstrictor and aldosterone. Secreting effects of angiotensin II by selectively blocking the binding of angiotensin II to the AT1 receptor found in many tissues (e.g., vasicular smooth muscle, adrenal gland) otherwise called as angiotensin receptor blockers (ARBs).

The present invention relates to a short, simple and practical process for the preparation of Losartan 1 which belongs to a novel class of tetrazole-imidazole compounds.

PRIOR ART

There are many processes recorded in literature. The latest prior art information for the preparation of Losartan is the disclosure made in the patent application of Novartis in their PCT WO 2005/014602 dated 17 Feb. 2005.

The process described in the application comprises the reaction of 4'-(Bromomethyl)-2-cyanobiphenyl (BromoOTBN) of the formula 3 with 2-n-butyl-4-chloro-5-formyl imidazole (BCFI) of the formula of 4 in the presence of Potassium carbonate and acetonitrile to give 'cyano aldehyde' of the formula 5. The Cyano aldehyde of the formula 5 is reduced with sodium borohydride to get 'cyano alcohol' of the formula 6. The Cyano alcohol is reacted with diethyl aluminium azide in the presence of triethyl aluminium to give Losartan of the formula 1.

The reaction scheme of the process is shown in the Scheme 1

Scheme 1

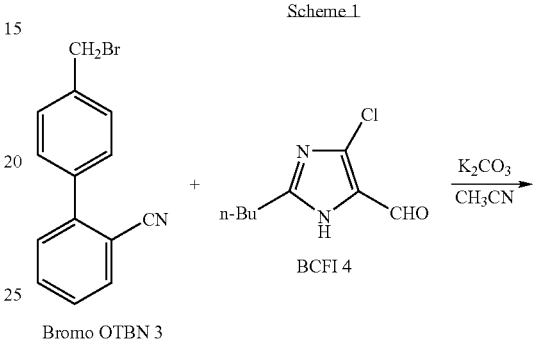

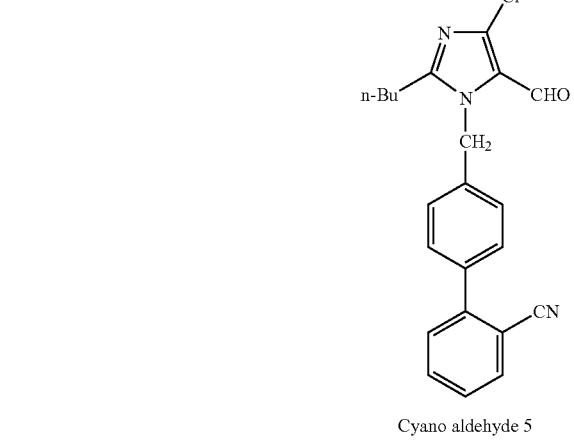

Even though the process is simple, handling of triethyl aluminium used needs special attention like very anhydrous conditions, reactions are to be performed under nitrogen or argon and transferring of triethyl aluminium from the containers needs anhydrous systems. The neat liquid and dense solutions of triethyl aluminium are known to ignite very easily at room temperature in presence of air (Pyrophoric). So handling of both triethyl aluminium and diethyl aluminium needs special attention like anhydrous conditions, nitrogen atmosphere etc., In EP 0578125A1 of Takeda Chemical Industries dated 12 Jan. 1994, yet another method for the preparation of Losartan has been disclosed in which Trioctadecyl or Trioctyl tin azide has been used as a tetrazole-forming agent. This method also uses the Cyano alcohol of the formula (6). The process comprises reacting the cyano alcohol of the formula (6) with tri-n-octyl tin azide in presence of toluene to give tri-n-octyl tetrazole derivative, which was treated with nitrous acid to give Losartan of the formula (1) in 94.7% yield. The process is shown in the reaction scheme 2

Scheme-2

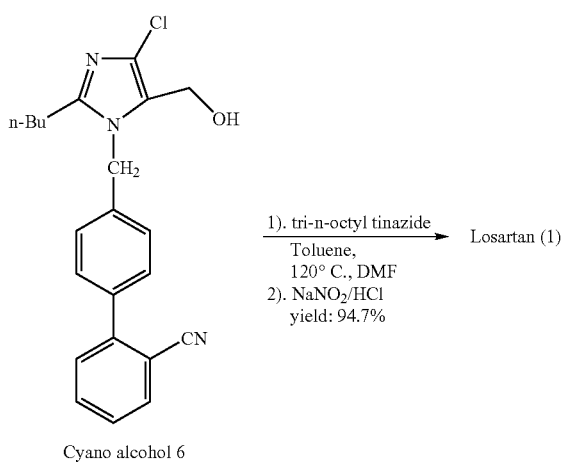

Cyano alcohol 6

Even though the yields are better (94.7%) in this process again handling of tri-n-octyl tin azide is involved.

Dupont/Merck in their patents and papers always described that trityl Losartan of the formula 7 is detritylated to get Losartan 1 For example they described in J. Med. Chem., 1991, 34, 2525-2547, the preparation of Losartan of the formula 1, from trityl Losartan of the formula 7 using mineral acids such as Hydrochloric acid and sulfuric acid in 93% yield. The reaction scheme of the process is shown in the scheme 3

Scheme-3

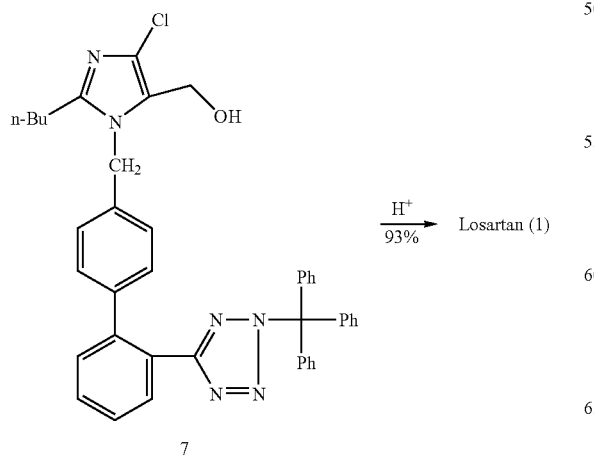

In this paper 'Aldehyde Tetrazole' of the formula 8 is isolated from trityl tetrazole aldehyde of the formula 21 and were further used for preparing derivatives of aldehyde such as benzene sulfonyl hydrazones of the formula 9 but not for Losartan. This process is shown in the scheme 4

Scheme 4

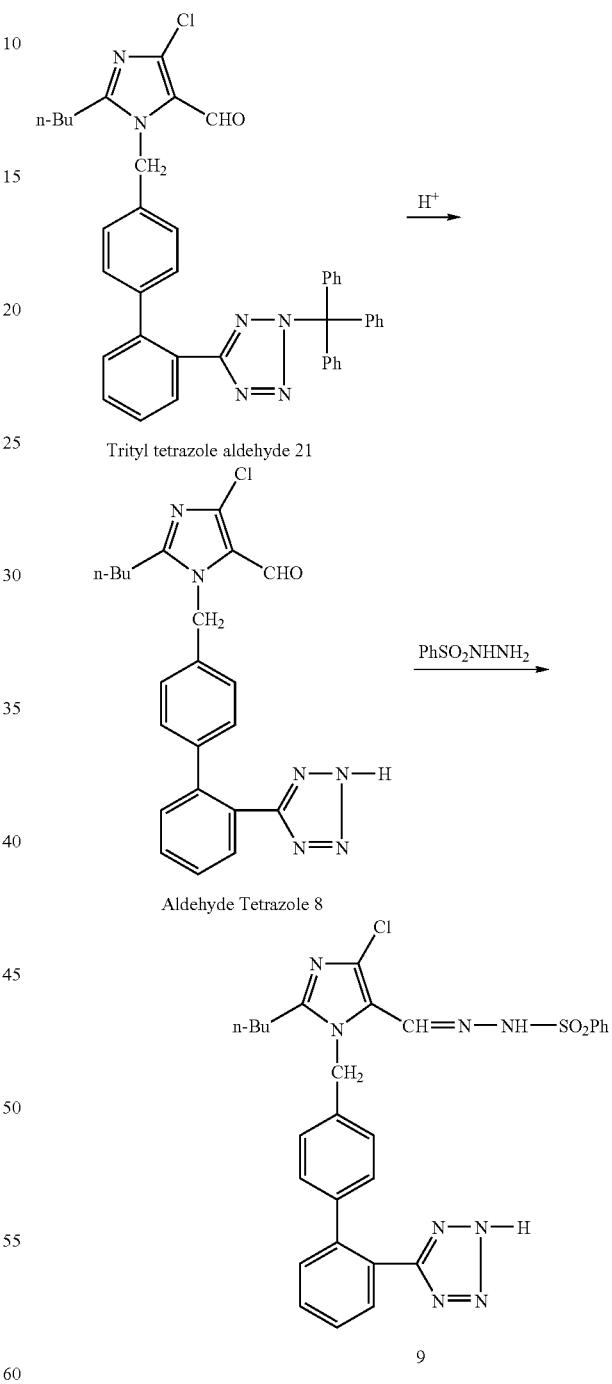

In J. Org. Chem 1994, 59, 6391-6394 again by Merck team reported Trityl Losartan and Losartan synthesis by coupling of boronic acid derivative 11 with 3-(4-bromobenzyl) derivative of BCBMI of the formula 10. The formed trityl Losartan of the formula 7 is converted to Losartan of the formula 1 with acid. The whole process is described in Scheme 5

Scheme 5

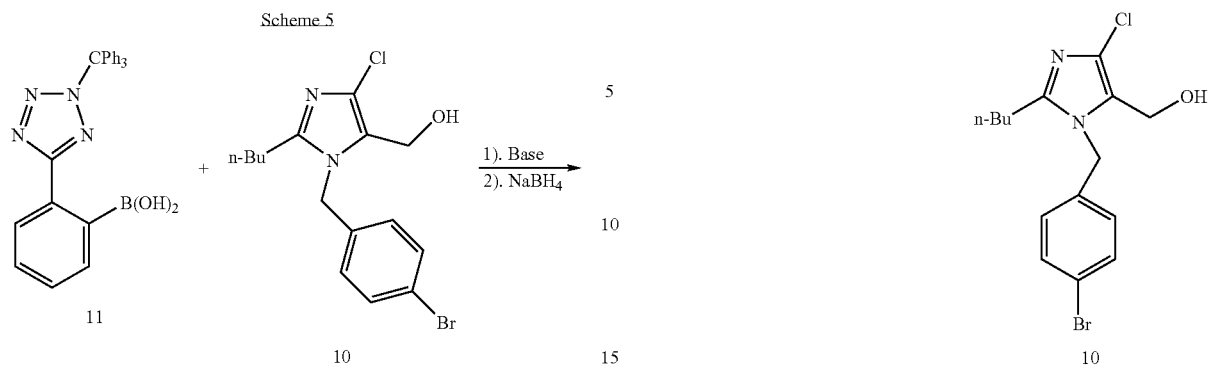

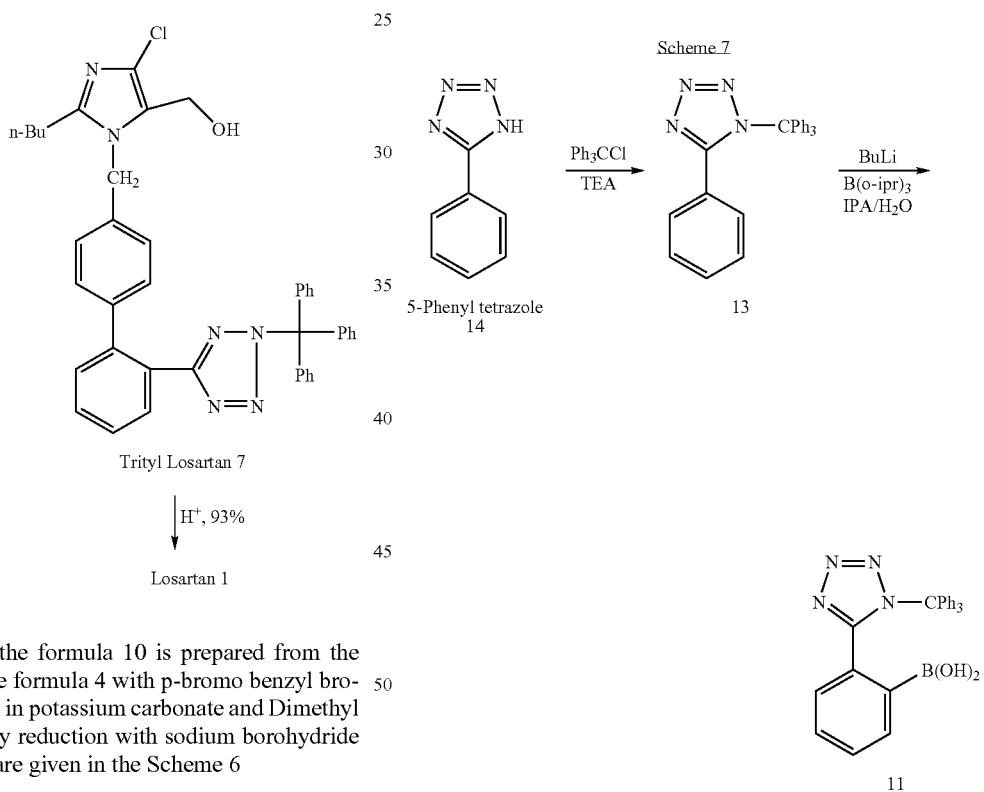

Trityl Losartan 7

↓ H⁺, 93%

Losartan 1

The Compound of the formula 10 is prepared from the reaction of BCFI of the formula 4 with p-bromo benzyl bromide of the formula 12 in potassium carbonate and Dimethyl formamide followed by reduction with sodium borohydride (NaBH₄). The details are given in the Scheme 6

The Compound of the formula 11 is prepared from 5-phenyl tetrazole of the formula 14 by reacting with trityl chloride to get N-trityl-5-phenyl tetrazole of the formula 13, which on reaction with butyl lithium and triisopropyl borate followed by hydrolysis to give compound of the formula 11. This process is shown in the Scheme 7

In one of the first patent filed by Dupont/Merck (date of filing 9 Jul. 1987, priority 11 January 1986 EP0253310) reported a procedure for the preparation of Losartan. Bromo OTBN of the formula 3 is reacted with BCHMI of the formula 15 in the presence of a base to give cyano alcohol of the formula 6, and its regioisomer of the formula 14. Separation of the isomer needs column chromatography. The cyano alcohol 6 is reacted with sodium/ammonium azide in DMF for 13 days to get Losartan 1 in 21% yield. The process is shown in the Scheme 8

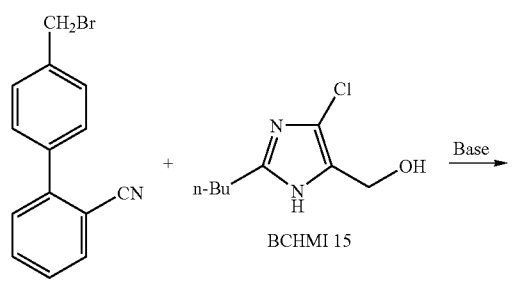

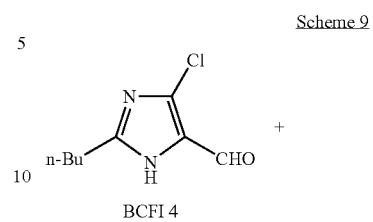

The process is shown in scheme 9

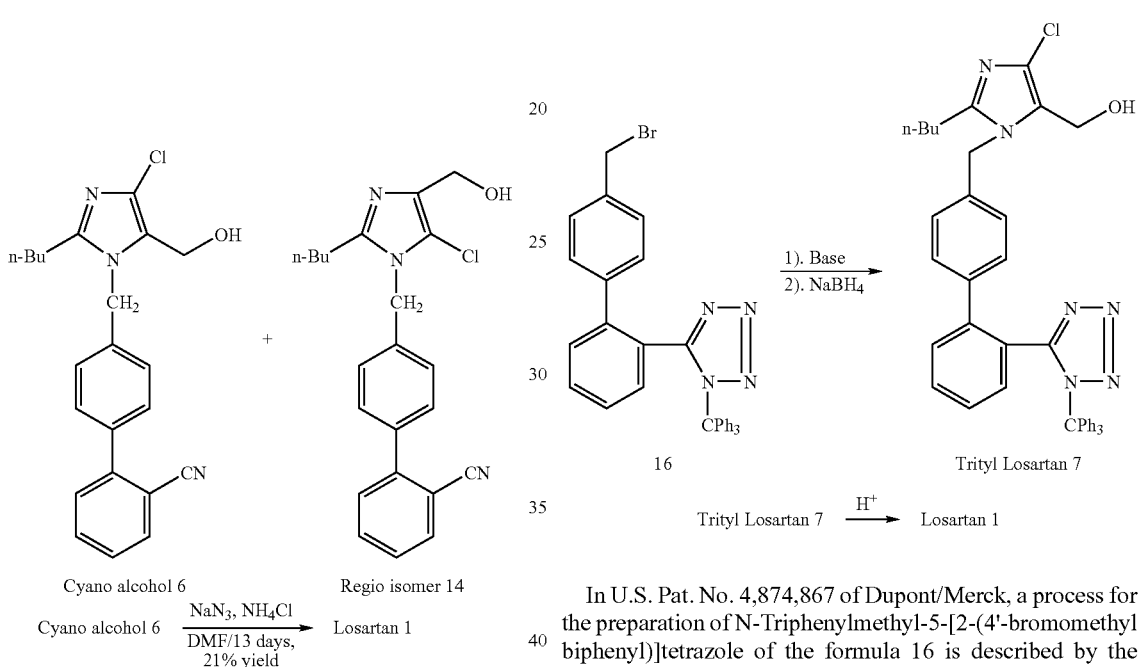

The drawbacks of the above process are
1). Separation of the regioisomer using column chromatography which is industrially not feasible for the preparation of large scale (ton) material/product
2). The tetrazole formation takes 13 days with 21% yield, which is unproductive.
3). Dupont/Merck uses BCHMI 15 as the starting material for preparing cyano alcohol of the formula 6. BCHMI 15 is an expensive intermediate compared to BCFI 4, and also the formation of unwanted regio isomer 14 is higher. The process is schematically described in scheme 8. Even though the process looks simple it has two problems.

First: Cyano alcohol is produced as a mixture of regioisomers and needs column chromatography for purification.

Second: Tetrazole formation. This takes 13 days with 21% yield, which limits commercialization of the process.

In U.S. Pat. No. 4,820,843 and U.S. Pat. No. 4,879,186, Dupont prepares Losartan by reaction of BCFI of the formula 4 and N-Triphenylmethyl-5-[2-(4'-bromomethyl biphenyl)] tetrazole of the formula 16 in the presence of base, followed by reduction with sodium borohydride to give Trityl Losartan of the formula 7, which is treated with mineral acid to give Losartan 1.

In U.S. Pat. No. 4,874,867 of Dupont/Merck, a process for the preparation of N-Triphenylmethyl-5-[2-(4'-bromomethyl biphenyl)]tetrazole of the formula 16 is described by the reaction of OTBN of the formula 20 with trimethyl tin azide to give the compound 17, which is treated with Hydrochloric acid to give tetrazole derivative of OTBN of the formula 18. The tetrazole derivative of OTBN of the formula 18 is protected with trityl chloride to give compound of the formula 19, followed by bromination with N-bromosuccinimide to give N-Triphenylmethyl-5-[2-(4'-bromomethyl biphenyl)] tetrazole of the formula 16.

The process is shown in the scheme 10.

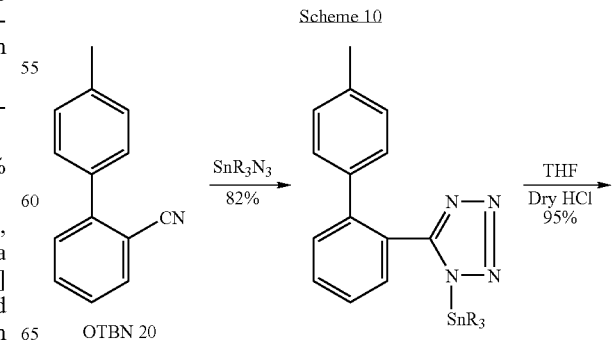

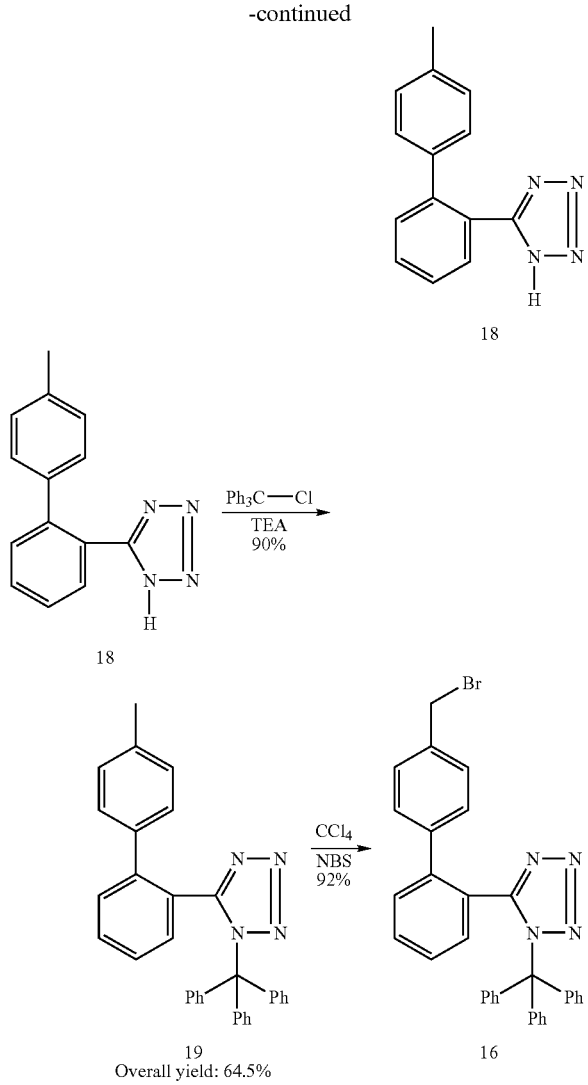

19
Overall yield: 64.5%

In all the above papers and patents by Dupont/Merck, the process yields in many steps are good 75-95% and in some steps are less to moderate 21-49%. The drawbacks, or the problems in all these processes is, the number of unit operations.

For example:
1). In J. Med. Chem 1991, 34, 2525-2547 the number of steps are six (6) to prepare Losartan of the formula 1 from the readily available intermediates.
2). In J. Org. Chem 1994, 59, 6391-6394 the number of steps are nine (9) to prepare Losartan of the formula 1 from the readily available intermediates.
3). In EP 0253310 patent the number of operations are two (2) but the problem is time & yields i.e., 13 days and poor yield (21%), also the uneconomical column chromatographic separation of regioisomer.
4). In U.S. Pat. Nos. 4,820,843 and 4,879,186 the number of steps are six (6).
5). In U.S. Pat. No. 4,874,867 the number of steps are seven (7).

Hence there is a continuous urge to develop a simple, short and improved process for the preparation of Losartan of the formula 1.

OBJECTIVES OF THE INVENTION

Accordingly the main objective of the present invention is to provide an improved process for the preparation of Losartan of the formula I given above overcoming the drawbacks of the hitherto known processes.

Another objective of the present invention is to provide an improved process for the preparation of Losartan of the formula I given above which is simple and environmentally friendly.

Still another objective of the present invention is to provide an improved process for the preparation of Losartan of the formula I given above in shorter reaction times.

Yet another objective of the present invention is to provide an improved process for the preparation of Losartan of the formula I given above in less number of steps to make it economical and with good yields. (>75%)

SUMMARY OF THE INVENTION

The improved three step process of the present invention starts with commercially available OTBN (Ortho toluoyl benzonitrile) of the formula 15. OTBN is reacted with DBDMH (dibromo dimethyl hydantoin) to give Bromo OTBN of the formula 3. The Bromo OTBN is reacted with BCFI of the formula 4 in presence of a base and phase transfer catalyst to give Cyanoaldehyde of the formula 5 in 83% yield. The cyanoaldehyde is reacted with sodium azide in the presence of tributyl tin chloride to give aldehyde tetrazole of the formula 8, which in situ reduced with sodium borohydride to give Losartan of the formula 1. The described process is shown in scheme 11

Scheme 11

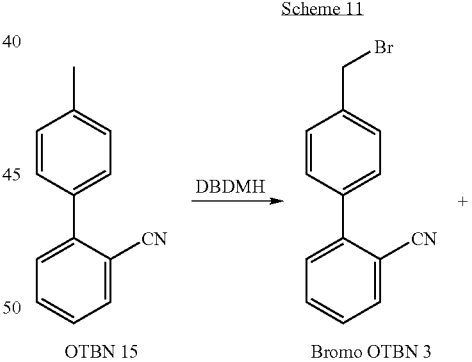

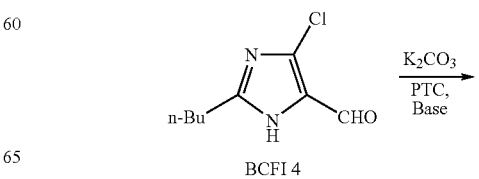

11
-continued
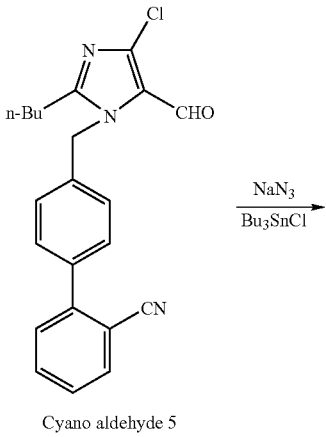
Cyano aldehyde 5
NaN₃ / Bu₃SnCl →
12
-continued
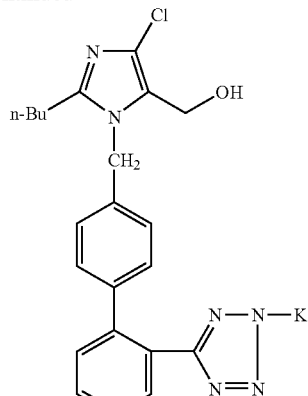
Losartan Potassium 2
Accordingly, the present invention provides an improved process for the preparation of Losartan of the formula 1
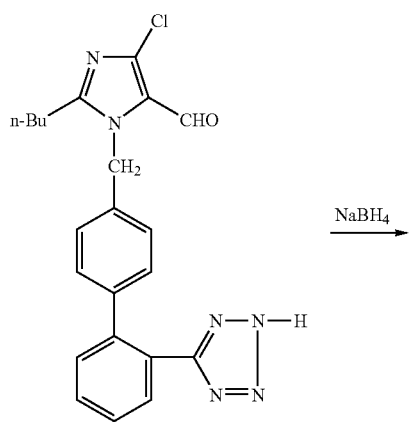
Aldehyde Tetrazole 8
NaBH₄ →
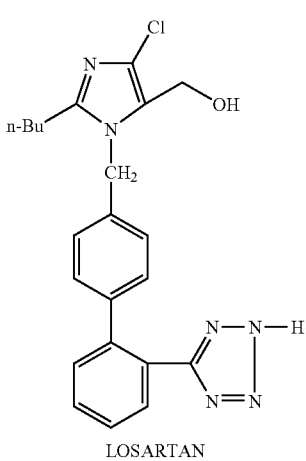
LOSARTAN
1
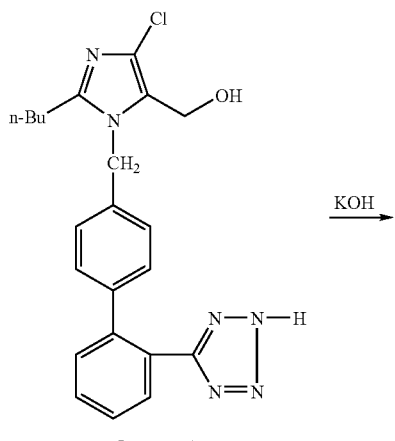
Losartan 1
KOH →
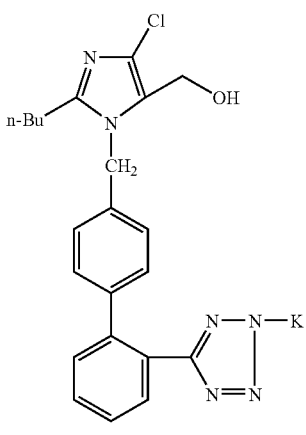
LOSARTAN POTASSIUM
2
and its potassium salt of the formula 2 which comprises (i) reacting bromo OTBN of the formula 3 with BCFI of the formula 4 in the presence of a base and a phase transfer catalyst to get cyano aldehyde of the formula 5

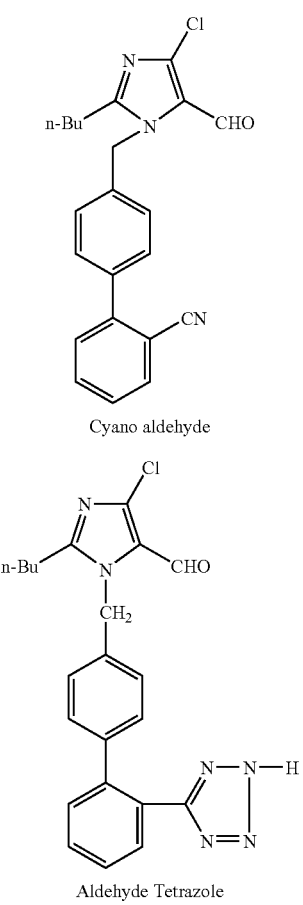

Cyano aldehyde

Aldehyde Tetrazole (ii) reacting the cyano aldehyde of the formula 5 formed with sodium azide in the presence of tributyl tin chloride to form aldehyde tetrazole of the formula 8, (iii) reducing the compound of the formula 8 with sodium borohydride to give Losartan of the formula 1 and (iv) if desired, converting it to its potassium salt by known methods.

The step (i) of the formation of cyano aldehyde may be carried out in the presence of phase transfer catalysts such as Tetrabutyl ammonium bromide (TBAB), or Benzyl triethyl ammonium chloride (TEBAC), Polyethylene Glycol (PEG—200, 400, 600, 800, 1000 etc.,), preferably Tetrabutyl ammonium bromide (TBAB), or Benzyl triethyl ammonium chloride (TEBAC), and most preferably in Tetrabutyl ammonium bromide (TBAB) to give cyano aldehyde of the formula 5.

In step (ii). Treating the cyano aldehyde of the formula 5 so formed with sodium azide and tributyl tin chloride may be carried out in an aromatic solvent to form tetrazole aldehyde of the formula 8 and converting to Losartan of the formula 1 with sodium borohydride in situ.

The formed tetrazole aldehyde in step (ii) may be reduced using Lithium Aluminium hydride, sodium borohydride, and Potassium borohydride preferably low cost Sodium borohydride.

The reaction temperature of step 11 for tetrazole formation may be between 90-150° C. preferably between 120-150° C. and most preferably between 140-150° C.

The details of the invention are given in examples given below which are provided by way of illustration only and therefore should not be construed to limit the scope of the invention

EXAMPLE-1

Preparation of Losartan Potassium. Step (I): Preparation of 1-(2'-Cyano biphenyl-4-methyl)-2-butyl-4-chloro-5-formyl imidazole of the formula 5 (Cyano aldehyde)

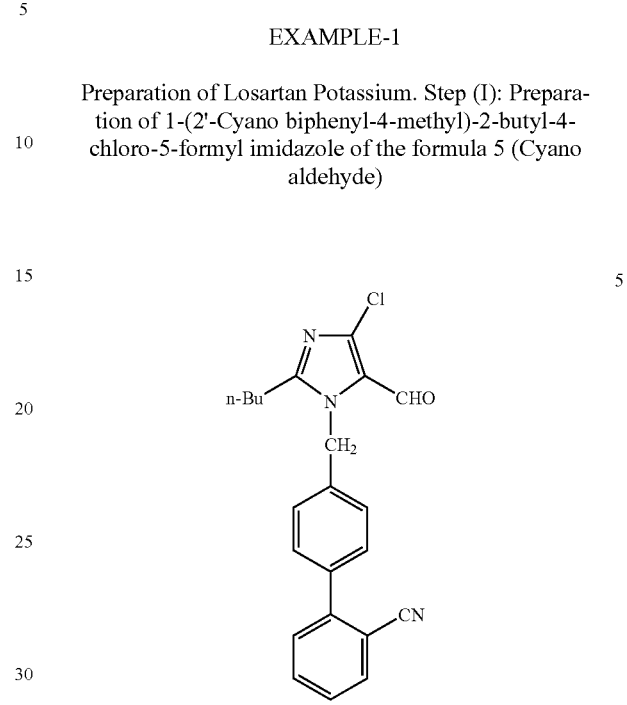

A solution of Benzoyl peroxide (3.6 g) and Carbon tetrachloride (180 ml) was slowly added to a suspension of Ortho tolyl benzonitrile (90 gm, 0.466 M), 1,3-Dibromo-5,5-dimethyl hydantoin (66 gm, 0.23M), Carbon tetrachloride (540 ml) at reflux temperature. (Exothermic, stop external heating during the addition of benzoyl peroxide solution). The reaction mixture was stirred for about 4 hours at reflux temperature. TLC Showed the absence of ortho tolyl benzonitrile. The precipitate was filtered, washed with carbon tetrachloride and dried. Solvent is evaporated under reduced pressure for about 3 hours at about 50° C. to give crude 4'-(Bromomethyl)-2-cyano biphenyl (Bromo OTBN). The crude 4'-(Bromomethyl)-2-cyano biphenyl (Bromo OTBN) used further without purification to produce cyano aldehyde of the formula 5.

To a stirred solution of Demineralised Water (360 ml), and sodium hydroxide flakes (14.4 gm, 0.36 M) was added toluene (900 ML), Tetrabutyl ammonium bromide (TBAB) (7.2 gm), 4'-(Bromomethyl)-2-cyano biphenyl (Bromo OTBN) (90 gm, 0.33 M) prepared as explained above and 2-butyl-4-chloro-5-formyl imidazole (65 gm, 0.34 M) at room temperature (25-30° C.). The solution was stirred at room temperature for 28-30 hours. After the reaction is completed by TLC, the organic layer is separated and the aqueous layer is extracted with 200 ml of toluene. The combined organic layers were washed with 150 ml of 7% sodium hydroxide solution and then finally washed with 200 ml of water. The Organic layer was concentrated to give a Crude Cyano aldehyde and was then triturated with Isopropyl alcohol to give Cyano aldehyde which is (1-(2'-Cyano biphenyl-4-methyl)-2-butyl-4-chloro-5-formyl imidazole) of the formula 5.

Yield 83%.

Melting point: 107-108° C.

HPLC Purity: >98%

IR. ν max (KBR): 2218 (—CN), 1662.40 (—CHO)

$^1$H NMR (CDCl$_3$) δ, 0.91 (t, 3H), 1.38 (sext, 2H), 1.73 (quint, 2H), 2.67 (t, 2H), 5.61 (s, 2H), 7.16-7.77 (m, 8H), 9.77 (s, 1H).

$^{13}$C NMR (CDCl$_3$) δ, 13.51, 22.18, 26.33, 29.04, 47.74, 110.05, 118.36, 124.11, 126.59, 127.65, 129.16, 129.81, 132.76, 133.61, 136.01, 137.69, 142.96, 144.33, 154.46, 177.73

Step-II: Preparation of 2-n-butyl-4-chloro-5-hydroxymethyl-1-[(2'-(1H-tetrazole-5-yl)biphenyl-4-yl)methyl]imidazole {Losartan} of the formula 1

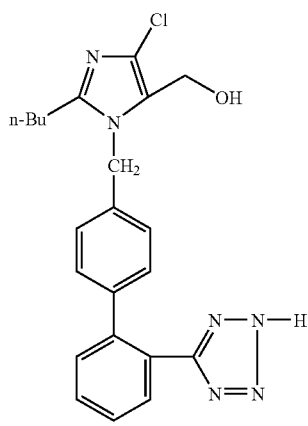

To a stirred solution of 1-(2'-Cyano biphenyl-4-methyl)-2-butyl-4-chloro-5-formyl imidazole (Cyano aldehyde) (100 gm, 0.264 M) prepared by the process described in step (I) in 210 ml of O-Xylene (800 ml) at room temperature was added Tri-n-butyl tin chloride (172 gm, 0.528 M) and sodium azide (34 gm, 0.523 M) at room temperature (25-30° C.). The reaction temperature was raised to 140-143° C. and maintained for 28-32 hours. TLC showed the absence of Cyano aldehyde. The reaction mixture was cooled to 25-30° C. and charged 1N aqueous KOH solution (2.0 Lts), and stirred for 1 hour at room temperature. The organic layer is separated and aqueous layer is washed with toluene (2×600 ml). Aqueous layer was proceeded further without isolation of aldehyde tetrazole. To the stirred solution of the aqueous layer (approximately ~2.2 Lts) was added sodium borohydride (9.0 gm, 0.238) at room temperature (25-30° C.). The reaction temperature is raised to 40-45° C. and maintained at this temperature for a period of 1 hour. TLC Showed the absence of aldehyde tetrazole. The reaction mass was cooled to 15-20° C. and the P$^H$ is adjusted to 4.0 with dilute HCl, stirred for 5-6 hours at 15-20° C. The cooled solution is filtered and washed with water to give Losartan of the formula 1.

Yield 75%
Melting point: 179-180.2
HPLC Purity: >97%
IR, ν max (KBR): 3376.27, 1579.77, 1468.86, 762.88, 556.4

$^1$H NMR (CDCl$_3$) δ, 0.87 (t, 3H), 1.31 (sext, 2H), 1.54 (quint, 2H), 2.57 (t, 2H), 4.45 (s, 2H), 5.30 (s, 2H), 7.01-7.68 (m, 8H).

$^{13}$C NMR (CDCl$_3$) δ, 14.07, 23.24, 27.40, 30.92, 126.71, 126.86, 127.35, 128.21, 130, 130.8, 131, 131.19, 131.81, 136.09, 142.21, 149.97, 162.72

MS (m/z)=423.5 (M+1).

Step-III: Preparation of 2-n-butyl-4-chloro-5-hydroxymethyl-1-[(2'-(1H-tetrazole-5-yl)biphenyl-4-yl)methyl]imidazole: Losartan Potassium salt 2

To a stirred solution of 2-n-butyl-4-chloro-5-hydroxymethyl-1-[(2'-(1H-tetrazole-5-yl)biphenyl-4-yl)methyl]imidazole (Losartan acid) (50 gm, 0.118 M) obtained by the process described in step (II) in 250 ml of methanol was added potassium hydroxide powder [7.6 gm (86%), 0.118 M] at room temperature (25-30° C.). The reaction temperature was raised to reflux (60-63° C.) and maintained for 4-5 hours at 60-63° C. The reaction mixture was cooled to 35-40° C. This was filtered through celite and the clarified solution was concentrated to remove most of methanol at 45-50° C. under reduced pressure. 100 ml of Methyl ethyl ketone was added and distillation continued to distill most of the methanol/methyl ethyl ketone mixture. Residue was diluted with 200 ml of Acetone and contents cooled to 5-10° C. for 30 minutes and product filtered and washed with 50 ml of acetone. Product was dried under reduced pressure to yield 47.5 grams. (87.15% of theory) Losartan Potassium.

HPLC Purity: 99.79%.
IR ν max (KBR): 3201.01, 1580.73, 1460.18, 764.81, 540.09

$^1$H NMR (MeOD) δ, 0.87 (t, 3H), 1.33 (sext, 2H), 1.53 (quint, 2H), 2.56 (t, 2H), 4.43 (s, 2H), 5.24 (s, 2H), 6.89-7.53 (m, 8H).

$^{13}$C NMR (MeOD) δ, 14.07, 23.24, 27.40, 30.92, 126.71, 126.86, 127.35, 128.21, 130, 130.8, 131, 131.19, 131.81, 136.09, 142.21, 149.97, 162.72

MS (m/z)=423.3 (M+1).

EXAMPLE-2

Preparation of Losartan Potassium

Step (I): Preparation of 1-(2'-Cyano biphenyl-4-methyl)-2-butyl-4-chloro-5-formyl imidazole of the formula 5 (cyano aldehyde)

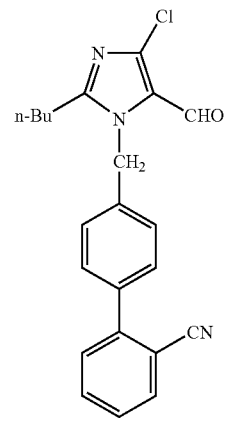

A solution of Benzoyl peroxide (3.6 g) and Methylene chloride (180 ml) was slowly added to a suspension of Ortho tolyl benzonitrile (90 gm, 0.466 M), 1,3-Dibromo-5,5-dimethyl hydantoin (66 gm, 0.23M), Methylene chloride (540 ml) at reflux temperature. (Exothermic, stop external heating during the addition of benzoyl peroxide solution). The reaction mixture was stirred for about 4 hours at reflux temperature. TLC Showed the absence of ortho tolyl benzonitrile. The precipitate was filtered, washed with Methylene chloride and dried. solvent is evaporated under reduced pressure for about 3 hours at about 50° C. to give crude 4'-(Bromomethyl)-2-cyano biphenyl (Bromo OTBN). The Crude 4'-(Bromomethyl)-2-cyano biphenyl (Bromo OTBN) was used further without purification to produce cyano aldehyde of the formula 5

To a stirred solution of Demineralised Water (360 ml), sodium hydroxide flakes (14.4 gm, 0.36 M) was added toluene (900 ML), Benzyl triethyl ammonium chloride (TEBAC) (7.2 gm), 4'-(Bromomethyl)-2-cyano biphenyl (Bromo OTBN) (90 gm, 0.33 M) obtained by the process described above and 2-butyl-4-chloro-5-formyl imidazole (65 gm, 0.34 M) at room temperature (25-30° C.). The solution was stirred at room temperature for 28-30 hours. After TLC completed the reaction, the organic layer was separated and the aqueous layer was extracted with 200 ml of toluene. The combined organic layers were washed with 150 ml of 7% sodium hydroxide solution and then finally washed with 200 ml of water. The Organic layer was concentrated to give a Crude Cyano aldehyde and is then triturated with Isopropyl alcohol to give 1-(2'-Cyano biphenyl-4-methyl)-2-butyl-4-chloro-5-formyl imidazole (which is Cyano aldehyde) of the formula 5.

Yield 83%, HPLC Purity: >98%

Step-II: Preparation of 2-n-butyl-4-chloro-5-hydroxymethyl-1-[(2'-(1H-tetrazole-5-yl)biphenyl-4-yl)methyl]imidazole (Losartan) of the formula 1

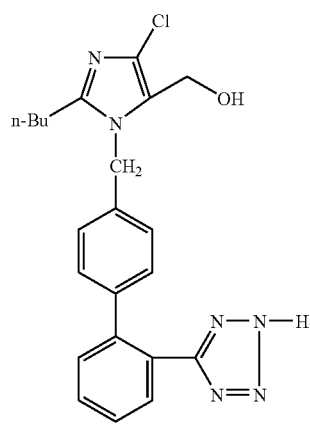

To a stirred solution of 1-(2'-Cyano biphenyl-4-methyl)-2-butyl-4-chloro-5-formyl imidazole (100 gm, 0.264 M) prepared by the process described in step (II) in 210 ml of O-Xylene (800 ml) at room temperature was added Tri-n-butyl tin chloride (172 gm, 0.528 M) and sodium azide (34 gm, 0.523 M) at room temperature (25-30° C.). The reaction temperature was raised to 140-143° C. and maintained for 28-32 hours. TLC showed the absence of cyano aldehyde. The reaction mixture was cooled to 25-30° C. and charged 1N aqueous KOH solution (2.0 Lts), and stirred for 1 hour at room temperature. The organic layer was separated and aqueous layer was washed with toluene (2×600 ml). Aqueous layer was proceeded further without isolation of aldehyde tetrazole. To the stirred solution of the aqueous layer (approximately ~2.2 Lts) was added sodium borohydride (9.0 gm, 0.238 M) at room temperature (25-30° C.). The reaction temperature is raised to 40-45° C. and maintained at this temperature for a period of 1 hour. TLC Showed the absence of aldehyde tetrazole. The reaction mass was cooled to 15-20° C. and the $P^H$ is adjusted to 4.0 with dilute HCl, stirred for 5-6 hours at 15-20° C. The cooled solution is filtered and washed with water to give Losartan of the formula 1.

Yield 75%

HPLC Purity: >97%

Step-III: Preparation of 2-n-butyl-4-chloro-5-hydroxymethyl-1-[(2'-(1H-tetrazole-5-yl)biphenyl-4-yl)methyl]imidazole: Losartan Potassium salt. 2

To a stirred solution of 2-n-butyl-4-chloro-5-hydroxymethyl-1-[(2'-(1H-tetrazole-5-yl)biphenyl-4-yl)methyl]imidazole (Losartan acid) (50 gm, 0.118 M), prepared by the process described in step (III) in 250 ml of methanol was added potassium hydroxide powder [7.6 gm (86%), 0.118 M] at room temperature (25-30° C.). The reaction temperature is raised to reflux (60-63° C.) and maintained for 4-5 hours at 60-63° C. The reaction mixture is cooled to 35-40° C. This was filtered through celite and the clarified solution was concentrated to remove most of methanol at 45-50° C. under reduced pressure. 100 ml of Methyl ethyl ketone was added and distillation continued to distill most of the methanol/methyl ethyl ketone mixture. Residue was diluted with 200 ml of Acetone and contents cooled to 5-10° C. for 30 minutes and product filtered and washed with 50 ml of acetone. Product was dried under reduced pressure to yield 47.5 grams. (87.0% of theory) Losartan Potassium.

ADVANTAGES OF THE INVENTION

1. The process is simple, economical, safe and commercially applicable
2. The process employs easily available materials like OTBN (Ortho tolyl benzonitrile or 2-(4-methyl phenyl) benzonitrile and BCFI (2-n-butyl-4-chloro-5-formyl imidazole).
3. Cyano aldehyde of the formula 5 is isolated as pure solid compound (>98% purity) and therefore the final product namely Losartan is also of high purity >99%.
4. Aldehyde Tetrazole of the formula 8 is prepared and reduced insitu to produce Losartan of the formula 1 of high purity >99%.

We claim:
1. A process for the preparation of Losartan of the Formula 1:

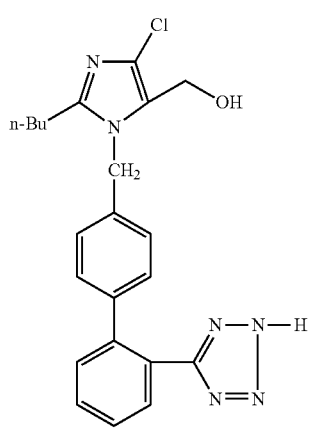

Formula 1 the process comprising:

(i) reacting bromo OTBN of the Formula 3:

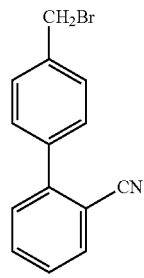

Formula 3 with BCFI of the Formula 4:

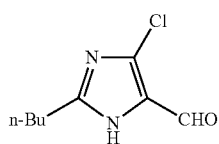

Formula 4 in the presence of a base and a phase transfer catalyst to form a cyano aldehyde of the Formula 5:

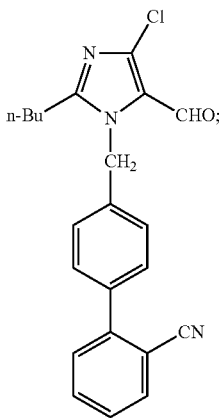

Formula 5

(ii) reacting the cyano aldehyde of the Formula 5 with sodium azide in the presence of tributyl tin chloride to form an aldehyde tetrazole of the Formula 8:

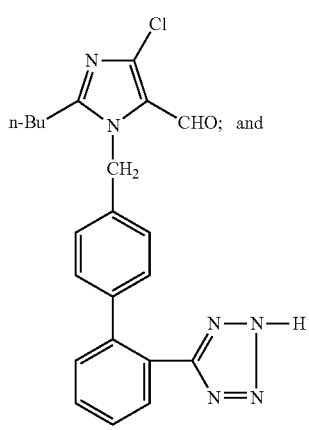

Formula 8

(iii) reducing the aldehyde tetrazole of the Formula 8 with at least one reducing agent selected from the group consisting of: lithium aluminum hydride, sodium borohydride, and potassium borohydride to form Losartan of the Formula 1.

2. The process as claimed in claim 1 wherein the phase transfer catalyst in step (i) is selected from the group consisting of: tetrabutyl ammonium bromide, benzyl triethyl ammonium chloride, and polyethylene glycol.

3. The process as claimed in claim 1 wherein the treatment of the cyano aldehyde of the Formula 5 to form the aldehyde tetrazole of the Formula 8 in step (ii) is in the presence of an aromatic solvent and wherein the conversion of the aldehyde tetrazole of the Formula 8 to Losartan of the Formula 1 in step (iii) is performed with sodium borohydride in situ.

4. The process as claimed in claim 1 wherein the aldehyde tetrazole of the Formula 8 is reduced in step (iii) with sodium borohydride.

5. The process as claimed in claim 1 wherein the production of the aldehyde tetrazole of the Formula 8 in step (ii) is carried out at a temperature in the range of 90-150° C.

6. The process as claimed in claim 1 wherein the production of the aldehyde tetrazole of the Formula 8 in step (ii) is carried out at a temperature in the range of 120-150° C.

7. The process as claimed in claim 1 wherein the production of the aldehyde tetrazole of the Formula 8 in step (ii) is carried out at a temperature in the range of 140-150° C.

8. The process as claimed in claim 1 wherein the phase transfer catalyst of step (i) is tetrabutyl ammonium bromide.

9. The process as claimed in claim 1 wherein the phase transfer catalyst of step (i) is benzyl triethyl ammonium chloride.

10. The process as claimed in claim 1 wherein the phase transfer catalyst of step (i) is polyethylene glycol.

11. The process as claimed in claim 1 further consisting of producing a potassium salt of Formula 2:

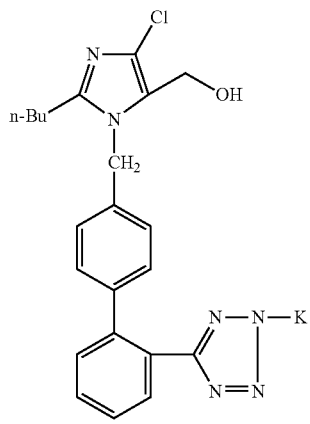

Formula 2 from the Losartan of Formula 1.

* * * * *